United States Patent [19]

Morita et al.

[11] Patent Number: 5,049,654

[45] Date of Patent: Sep. 17, 1991

[54] CALCITONIN GENE RELATED PEPTIDE DERIVATIVES

[75] Inventors: Kaoru Morita; Toyonobu Uzawa; Masayuki Hori; Toshiharu Noda, all of Shizuoka, Japan

[73] Assignee: Toyo Jozo Kabushiki Kaisha, Shizuoka, Japan

[21] Appl. No.: 128,950

[22] Filed: Dec. 4, 1987

[30] Foreign Application Priority Data

Dec. 4, 1986 [JP] Japan .................................. 61-289597
Dec. 25, 1986 [JP] Japan .................................. 61-310585

[51] Int. Cl.$^5$ ............................................... C07K 7/36
[52] U.S. Cl. ..................................... 530/307; 530/317; 530/324
[58] Field of Search ........................ 530/307, 317, 324

[56] References Cited

U.S. PATENT DOCUMENTS 4,743,677  5/1988  Noda et al. ......................... 530/307

FOREIGN PATENT DOCUMENTS

WO85/00165  1/1985  Int'l Pat. Institute .

OTHER PUBLICATIONS

Sako et al., *Chem. Ab.*, 1987, 107(34), ab #7563x, *Pept. Chem.*, 1986 pub.

"Isolation and Characterization of Human Calcitonin Gene-Related Peptide", *Nature*, vol. 308, No. 19, Apr. 1984, by H. Morris, et al., pp. 746-748.

"Calcitonin Gene-Related Peptide is a Potent Vasodilator", *Nature*, vol. 313, No. 3, Jan. 1985, by S. Brain et al., pp. 54-56.

"The Myotropic and Plasma-Calcium Modulating Effects of Calcitonin Gene-Related Peptide (CGRP)", *Neuropeptides*, vol. 4, 1984, by J. Tippins et al., pp. 425-434.

"Studies on Peptides, CXLII, 1.2) Synthesis of Des-1-Ala-des-α-amino-Human Calcitonin Gene-Related Peptide", *Chem. Pharm. Bull.*, vol. 34, No. 9, Sep. 1986, by A. Otaka et al., pp. 3915-3918.

"Isolation and Partial Characterization of the Calcitonin Gene in a Lower Vertebrate", *Febs Letters*, vol. 203, No. 1, Jul. 1986; by S. Minvielle et al., pp. 7-10.

*Primary Examiner*—Johnnie R. Brown
*Assistant Examiner*—Stephen B. Maebius
*Attorney, Agent, or Firm*—Young & Thompson

[57] ABSTRACT

A compound of the formula

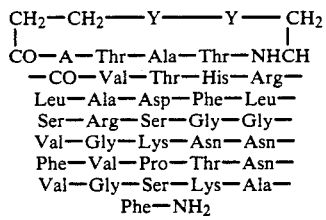

wherein Y is sulfur or methylene and A is Asn or Asp, or a pharmaceutically acceptable salt thereof is useful for the treatment of calcium metabolic disorders, cardiac disease and ulcers, and for the improvement of cranial circulation.

5 Claims, 4 Drawing Sheets

CALCITONIN GENE RELATED PEPTIDE DERIVATIVES

FIELD OF THE INVENTION

This invention relates to novel chicken calcitonin gene related peptide (hereinafter designated as c-CGRP) derivatives, useful for the treatment of calcium metabolic disorders, cardiac disease and ulcers, and for the improvement of cranial circulation.

THE KNOWN PRIOR ART

Recently, the amino acid sequence of c-CGRP has been elucidated by analysis of the DNA sequence of chickens [FEBS Letters, Vol. 203, No. 1, 7–10, July 1986].

SUMMARY OF THE INVENTION

No report is known, of the isolation and synthesis of c-CGRP, and hence the activity of c-CGRP was not known. Therefore, it is important in the medical field to synthesize the c-CGRP derivatives and to compare their biological activity with that of the known CGRP.

We have synthesized various derivatives of c-CGRP and have made comparative studies of their biological activities. As a result, we have found that they have stronger serum calcium reducing activity and serum phosphate reducing activity with a superior prolonged action, as compared with human CGRP (hereinafter designated h-CGRP). [Nature, 308 (19): 746–748 (1984), Neuropeptides, 4: 425–434 (1984), Nature, 313 (3): 54–56 (1984)].

More particularly, the present invention provides novel c-CGRP derivatives of the formula wherein Y is sulfur or methylene and A is Asn or Asp, or a pharmaceutically acceptable salt thereof.

In the present invention, a peptide [1] wherein Y is sulfur and A is Asn is designated desalanyl-deamino c-CGRP, and a peptide [1] wherein Y is sulfur and A is Asp is designated desalanyl-deamino-[Asp³]-c-CGRP. A peptide [1] wherein Y is methylene and A is Asn is designated desalanyl-[Asu$^{2,7}$]-c-CGRP, and a peptide wherein Y is methylene and A is Asp is designated desalanyl-[Asp³, Asu$^{2,7}$]-c-CGRP.

A peptide [1] of the present invention can be synthesized by a known conventional process for peptide synthesis.

(1) A process by liquid phase synthesis:

When Y is sulfur, peptide [1] is synthesized by converting a carboxyl in phenylalanyl in the C-terminal to an amide, condensing successively a protected amino acid and/or a protected lower peptide in the order of amino acid sequence as shown in the formula [1], removing the protective group for L-cystinyl and mercapto in β-mercaptopropionic acid and the protective group for the functional group in the other side chain by acid hydrolysis, and oxidizing mercapto to form a disulfide bridge at a final stage of the condensation reaction.

When Y is methylene, the peptide [1] is synthesized by converting a carboxyl in phenylalanyl in the C-terminal to an amide, condensing successively a protected amino acid and/or a protected lower peptide in the order of the amino acid sequence as shown in formula [1], subjecting the construction unit containing the thus-formed fragment of the formula wherein R is an activated ester residue and A has the same meaning hereinbefore, to a cyclization reaction at a required stage of the above condensation reaction, and removing the protective groups for the active group by acid hydrolysis at the final stage of the condensation reaction.

The condensation reaction can be effected by repeating the removal and addition of a protective group and the condensation reaction according to the process for conventional peptide synthesis. A protective group for a starting material and intermediates used in the process for the production of a peptide [1] of the present invention is a known protective group in peptide chemistry, for example a peptide which can be easily removed by a known procedure such as hydrolysis, acid decomposition, reduction, aminolysis or hydrazinolysis. These protective groups are well known in the literature of peptide chemistry.

Examples of preferred protective groups are butyloxyl carbonyl, benzyloxy carbonyl or p-methoxybenzyloxy carbonyl for a α-amino group, benzyloxy carbonyl or p-chlorobenzyloxy carbonyl for a side chain amino group such as ε-amino in lysine, a methyl ester or benzylester for an α-carboxyl group, benzyl ester for a side chain carboxyl group such as the side chain carboxyl in aspartic acid, a t-butyl ester for the side chain carboxyl in α-aminosuberic acid, benzyl for a hydroxyl group in serine or threonine, and methylene-2-sulfonyl or tosyl for the amino group of guazinino in arginine.

In the synthesis of a peptide [1] of the present invention, the condensation of each amino acid and/or lower peptide can be effected by reacting an amino acid or a lower peptide having protected α-amino and activated terminal α-carboxyl, with an amino acid or a lower peptide having free α-amino and a protected terminal carboxyl group, or alternatively by reacting an amino acid or a lower peptide having activated α-amino and protected terminal carboxyl with an amino acid or a lower peptide having a protected terminal carboxyl group.

A carboxyl group can be activated by conversion, for example to acid azide, acid anhydride, acid imidazolide or an activated ester such as cyanomethyl ester, p-nitrophenyl ester or N-hydroxysuccinimide ester. Furthermore, it can be activated by using a condensation reagent, for example a carbodiimide such as N,N'-dicyclohexyl-carbodiimide (DCCD), N-ethyl-N'-3-dimethylaminopropyl-carbodiimide or N,N'-carbonyldiimidazole.

Examples of preferred condensation reactions used in the present invention are the azide method, the activated ester method, the mixed anhydride method and the carbodiimide method. In the condensation reaction, it is preferred to avoid or at least to minimize the racemization reaction; and preferred such processes are the azide method, the activated ester method, the Wunsch method [Z. Naturforsch., 21b, 426 (1966)] or the Geiger method [Chem. Ber., 103, 788 (1970)].

A peptide [1] can be synthesized in any sequence; however, it is preferable to construct an amino acid sequence by connecting amino acid and/or lower peptide in order from the C-terminal.

A further process for obtaining peptide [1] from the thus-synthesized protected peptide chain depend on the structure of the peptide [1] wherein Y is sulfur or Y is methylene.

A peptide [1] wherein Y is sulfur can be obtained by removing the protective groups in the protected peptide chain, namely β-mercaptopropionyl pentatriaconta-peptideamide having protected ω-amino, side chain carboxyl, hydroxyl, guanidino and mercapto groups. These protective groups are preferably removed by one-step removal with acid hydrolysis using for example trifluoromethane sulfonic acid or anhydrous hydrogen fluoride to obtain β-mercaptopropionyl pentatriaconta-peptideamide having a free mercapto group.

In the said peptide-amide, an inner molecular disulfide linkage is formed by oxidation to obtain the peptide [1]. Disulfide linkage can be effected generally by oxidation with oxygen in water, diiodo-ethane in an organic solvent, iodine in glacial acetic acid or potassium ferricyanide in water.

When Y is methylene, the construction unit of the formula wherein R and A have the same meanings hereinbefore, is subjected to a cyclization reaction at any stage of the condensation reaction during protected peptide chain synthesis. The cyclization can be effected by a condensation reaction with the ω-carboxyl group in α-aminosuberic acid and the free amino group in an N-terminal amino acid. In the said reaction, hydroxyl in threonine and side chain carboxyl in aspartic acid are preferably protected.

The thus-obtained cyclic peptide having a protected or unprotected activated group and a large peptide having a protected or unprotected activated group are condensed, and if there is a protected group, the protective group is removed.

Thus pentatriaconta peptide-amide having protected ε-amino, side-chain carboxyl, guanidino and hydroxyl groups can be obtained. These protective groups are preferably removed by acid hydrolysis such as a method using trifluoromethane sulfonate and anhydrous hydrogen fluoride in a onestep removal method to obtain the peptide [1].

(2) A process by solid phase synthesis

In the present invention, a solid phase peptide synthesis method can be used in part or in toto as the process of peptide [1] synthesis.

For example, in the case of the synthesis of peptide [1] wherein Y is sulfur, a peptide fragment (3-37) [hereinafter peptide of amino acid sequence constituted of amino acids from Nos. 3 to 37 is abbreviated as peptide fragment (3-37) or peptide (3-37)] is synthesized by a solid phase method, and the α-amino group in the said peptide is acylated with β-mercaptopropionic acid to obtain a protected pentatriaconta-peptide-bound resin. These protective groups and the resin are removed by a known method such as using trifluoromethane sulfonic acid or anhydrous hydrogen fluoride in a one-step removal to obtain a β-mercaptopropionyl pentatriaconta peptide-amide having a free mercapto group. A peptide [1] can be obtained by constructing an inner molecule disulfide bond as set forth in the process by liquid phase synthesis (1) hereinabove.

Furthermore, in the case of the synthesis of a peptide [1] wherein Y is methylene, a peptide fragment (9-37) is synthesized by the solid phase method, and a cyclic peptide fragment containing N-terminal α-aminosuberic acid is synthesized by the liquid phase method. Subsequently, the above two peptide fragments are condensed by the solid phase method to obtain a protected pentatriaconta-peptide-bound resin. These protective groups and this resin are removed by a known method such as using trifluoromethane sulfonic acid or anhydrous hydrogen fluoride in a one-step removal to obtain the peptide [1].

Examples of resin used in the solid phase method are conventional resins such as benzhydrylamine resin or p-methyl-benzhydrylamine resin. A resin with the desired functional equivalent or cross-linkage can be synthesized but is also commercially available.

In the solid phase method, an amino acid is condensed, fragment by fragment, in the order of amino acid sequence of formula [1], from C-terminal amino acid to the third number of amino acid (amino acid No. 3) (in the case of a peptide wherein Y is sulfur), or from C-terminal amino acid to the 9th number of amino acid (amino acid No. 9) (in the case of a peptide wherein Y is methylene). A functional group in the amino acid is protected by a known method. Examples of protective groups are set forth hereinbefore.

In the solid phase reaction, a resin in a reaction vessel is swelled by adding dichloromethane, chloroform, dimethylformamide, benzene or a solvent for swelling the resin, in a ratio of 2–20 ml solvent per 1 g resin. In another reaction vessel, 1–6 equivalents of t-butyloxycarbonyl- (hereinafter designated Boc-) amino acid per 1 equivalent of amino group in the resin are first reacted with DCC, and the obtained acid anhydride, which is separated from a by-product dicyclohexylurea (hereinafter designated DCU), is added to the resin hereinabove. The amount of condensation agent (DCC) is 0.5–3 equivalents per 1 equivalent of Boc-amino acid. The reaction proceeds generally for 5–60 minutes.

The coupling amount of amino acid or peptide can be determined according to a conventional method [T. Fairwell et al., Biochemistry, 22: 2691 (1983)] by checking the amount of Boc-amino acid upon sampling the Boc-amino acid-resin or Boc-peptide-resin obtained in each process.

The protective group for the α-amino group, Boc, is removed by an acid such as trifluoroacetic acid and the condensation reaction is performed. An automatic solid phase synthesizer can be used; however, a manual procedure can also be used. The entire operation is preferably performed under a nitrogen gas atmosphere.

In this way, a peptide fragment (3-37) or (9-37) bound to a resin can be obtained.

A peptide fragment (3-37) bound to resin is acylated with β-mercaptopropionic acid in the final step to obtain a β-mercaptopropionyl-protected pentatriaconta peptide-amide-bound resin.

The thus-obtained protected pentatriaconta peptide-amide-bound resin is, as previously described, treated with anhydrous hydrogen fluoride to remove the protective group and resin in one step, whereby β-mercaptopropionyl pentatriaconta peptide-amide having a free mercapto group can be obtained.

A peptide [1] wherein Y is sulfur can be obtained by forming inner molecular disulfide bonds in the above β-mercaptopropionyl pentatriaconta peptide-amide having a free mercapto group.

In the synthesis of a peptide [1] wherein Y is methylene, a peptide fragment (9-37) bound resin is condensed with a cyclic peptide fragment containing α-aminosuberic acid.

The thus-obtained protected pentatriaconta bound resin containing α-aminosuberic acid is treated with anhydrous hydrogen fluoride to remove the protective group and resin in one step, leaving the peptide [1] wherein Y is methylene.

(3) Isolation and purification

Peptide [1] can be purified by a purification method which is well known in peptide or protein chemistry. For example, a gel-filtration method can be carried out using Sephadex G-25, Sephadex G-50 or Sephadex LH-20 (trade names), or column chromatography using an ion-exchange resin or carboxy methyl cellulose, or HPLC can be used.

A peptide [1] of the present invention can be obtained according to the process in the form of free base or salt. For example a salt with a known organic acid such as acetic acid can be prepared.

The abbreviations in the specification and drawings are identified as follows:

| | |
|---|---|
| Asu: | L-α-aminosuberic acid |
| Asn: | L-asparagine |
| Asp: | L-aspartic acid |
| Ala: | L-alanine |
| Thr: | L-threonine |
| Val: | L-valine |
| His: | L-histidine |
| Arg: | L-arginine |
| Leu: | L-leucine |
| Phe: | L-phenylalanine |
| Ser: | L-serine |
| Gly: | glycine |
| Lys: | L-lysine |
| Pro: | L-proline |
| Boc: | t-butyloxycarbonyl |
| Z: | benzyloxycarbonyl |
| Cl-Z: | p-chlorobenzyloxycarbonyl |
| Bzl: | benzyl |
| OSu: | N-hydroxysuccinimide ester |
| ONp: | p-nitrophenyl ester |
| OMe: | methyl ester |
| OBut: | t-butyl ester |
| OBzl: | benzyl ester |
| TFA: | trifluoroacetic acid |
| Ether: | diethyl ether |
| DMF: | N,N'-dimethylformamide |
| MeOH: | methanol |
| DCM: | dichloromethane |
| DIEA: | diisopropyl ethylamine |
| HOBt: | 1-hydroxybenzo triazole |
| MBHA-resin: | p-methylbenzhydrylamine resin |

UTILITY OF THE INVENTION

Serum calcium and serum phosphate reducing activities:

Assay method

Desalanyl-deamino-c-CGRP, desalanyl-[Asu$^{2,7}$-c-CGRP and desalanyl-[Asp$^3$, Asu$^{2,7}$]-c-CGRP (each 80 μg), and c-CGRP (Japan. Patent Unexam. Publ. No. 61-273581) and known h-CGRP (each 80 μg for control group) dissolved in citrate buffer, pH 6.5, containing 0.1% bovine serum albumin (hereinafter designated dissolving medium) (1 ml) were administered intravenously into the tail vein of Wistar rats, body weight 80-90 g, 5-6 rats in one group, at 20 or 80 μg/kg. After 30 and 60 mins. of administration, blood samples were collected from the abdominal descending aorta. The serum calcium concentration was measured by atomic adsorption spectrophotometry. Serum phosphate was measured by a method according to Goldenberg et al. [Clin. Chem., 12: 872-882 (1966)].

RESULTS

Figure 1:
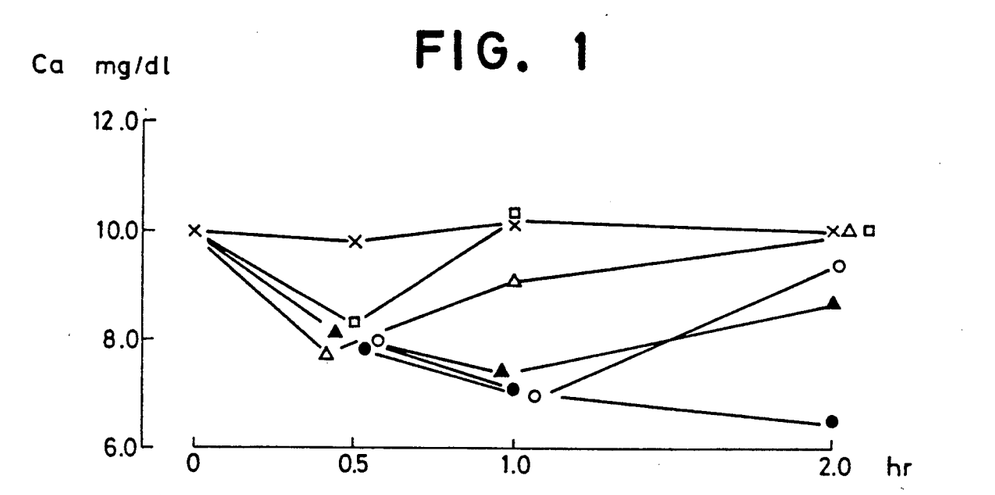
FIG. 1 is a graph showing the rat serum calcium reducing effect of h-CGRP, c-CGRP and desalanyl-deamino-c-CGRP of the present invention.
Figure 2:
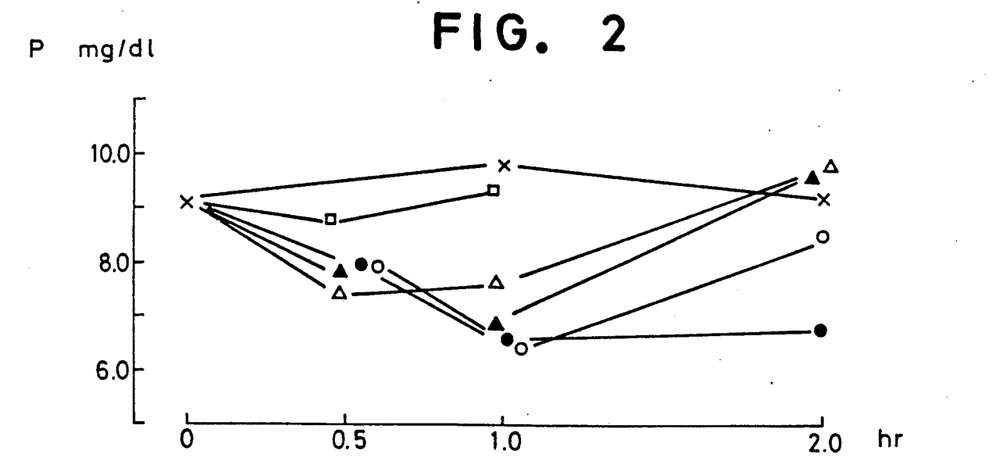
FIG. 2 is a graph showing the rat serum inorganic phosphate reducing effect of h-CGRP, c-CGRP and desalanyl-deamino-c-CGRP of the present invention.

As shown in FIGS. 1 and 2, the concentrations of serum calcium and phosphate were reduced by more than 30% in desalanyl-deamino-c-CGRP, 20 μg/kg, administered group (-○-) as compared with control group (dissolving medium administered group (-X-) and these activities were observed to continue after 2 hours. These activities were stronger than those of h-CGRP administered in quadruple the amounts (-□-, 80 μg/kg), and were significantly strong as compared with c-CGRP administered at the equivalent dosage level (-Δ-, 20 μg/kg), and the effects were prolonged significantly.

Further as shown in FIGS. 1 and 2, concentrations of serum calcium and phosphate were reduced by more than 30% in desalanyl-deamino-c-CGRP, 80 μg/kg, administered group (- -) as compared with control group (dissolving medium administered group) (-X-) and these activities were observed to continue after 2 hours; moreover, the serum calcium reducing activity was further enhanced. These activities were stronger than those of h-CGRP (-□-, 80 μg/kg) and c-CGRP (- -, 80 μg/kg) administered at equivalent dosage levels, and the effects were prolonged significantly.

Figure 3:
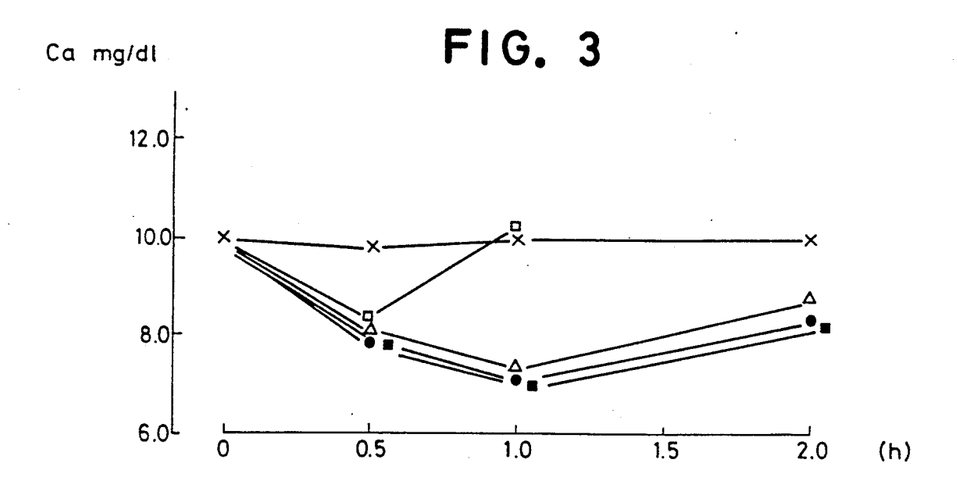
FIG. 3 is a graph showing the rat serum calcium reducing effect of h-CGRP, c-CGRP, desalanyl-[Asu$^{2,7}$]-c-CGRP and desalanyl-[Asp$^3$, Asu$^{2,7}$]-c-CGRP of the present invention.
Figure 4:
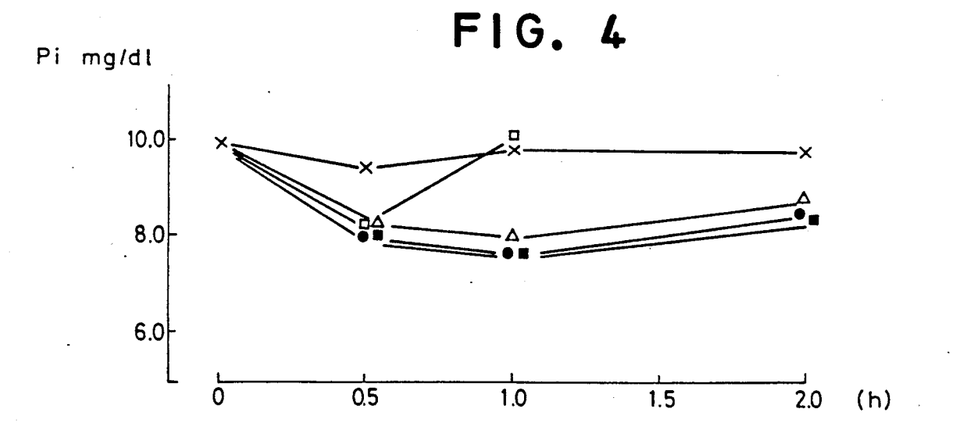
FIG. 4 is a graph showing the rat serum inorganic phosphate reducing effect of h-CGRP, c-CGRP, desalanyl-[Asu$^{2,7}$]-c-CGRP and desalanyl-[Asp$^3$,Asu$^{2,7}$]-c-CGRP of the present invention.

As shown in FIGS. 3 and 4, the concentrations of serum calcium and phosphate were reduced by more than 30% in the groups in which were administered desalanyl-[Asu$^{2,7}$]-c-CGRP, 80 μg/kg (- -) and desalanyl-[Asp$^3$,Asu$^{2,7}$]-c-CGRP, 80 μg/kg (- -), as compared with the control group (dissolving medium administered group) (-X-) and these activities were observed to continue more than 2 hours. These activities were stronger than that of h-CGRP administered in equivalent amounts (-□-, 80 μg/kg), and were significantly strong as compared with c-CGRP administered in an equivalent dose (-Δ-, 20 μg/kg), and the effects were prolonged significantly.

As illustrated hereinabove, the peptide [1] of the present invention has stronger serum calcium reducing activity and serum phosphate reducing activity as compared with known h-CGRP. Furthermore, it has longer-sustained activity and has stronger biological activity with longer-sustained activity as compared with c-CGRP. Moreover, it is stable against the action of amino-peptidase in vivo, and hence is useful for treatment of calcium metabolic disorders, cardiac disease and ulcers, or for the improvement of cranial circulation.

The following examples illustrate the present invention.

In the examples, PF( ) means a peptide fragment having an amino acid sequence order of ( ) numbers.

The carriers and developers used in thin layer chromatography (TLC) and the condition of hydrolysis in amino acid analysis are illustrated, if not specified, as follows:

TLC:
  Carrier: silica-gel (Merck, Art 5715)
  Developer: 1; chloroform:methanol:acetic acid (95:5:3) 2; chloroform:methanol:acetic acid (85:15:5)
Hydrolysis:
  Samples were hydrolyzed at 110° C. for 24–48 hours with HCl in a sealed tube.

EXAMPLE 1

Production of desalanyl-[Asu$^{2,7}$]-c-CGRP: Anisole (1 ml) was added to desalanyl-[Asu$^{2,7}$]-protected-c-CGRP (3-37)-MBHA-resin of the formula

(1.09 g). Anhydrous hydrogen fluoride (25 ml) was added thereto and the mixture was stirred at 0° C. for 1 hour. After the anhydrous hydrogen fluoride was distilled off in vacuo, the residue was washed with ether and 0.1 M acetic acid (20 ml) was added thereto to extract the peptide. The extract was passed through a Dowex WGR (trademark) column (2.8×15 cm) and eluted with 0.1 M acetic acid (60 ml). The eluate was freeze dried to obtain a white powder (370 mg). This powder was charged on a column of carboxymethyl cellulose (2.8×13 cm) and was subjected to linear gradient elution with 0.01 M aqueous ammonium acetate (pH 4.5, 300 ml)∼0.5 M aqueous ammonium acetate (pH 5.3, 300 ml). Samples (100 μl) from the fractions (each 10 ml) were measured colorimetrically by the Folin-Lolly method at 750 nm. Fractions Nos. 33–37 were collected and charged on a column (2.3×5.5 cm) of CHP-20 resin (trademark, Mitsubishi Kasei Kogyo), and eluted by linear gradient elution with 0.1 M aqueous acetic acid containing 25% acetonitrile (150 ml)∼0.1 M aqueous acetic acid containing 40% acetonitrile (150 ml). Fractions (each 6.4 ml) Nos. 10–12 were collected and freeze dried to obtain a white powder (30.5 mg). This powder was purified by reverse phase HPLC to obtain purified desalanyl-[Asu$^{2,7}$]-c-CGRP (3.4 mg).

Column: Nucleosil 5C$_{18}$
  Buffer: 0.1% TFA-acetonitrile (a gradient elution with acetonitrile concentration from 28 to 38% for 25 minutes)
  Flow: 2.5 ml/min.
  Fraction: collected at a peak at retention time 17.8 min.
  Physical properties: pI: more than 10.25
  $[\alpha]_D^{26.5}$: −53.3 (c=0.094, 0.1 M acetic acid).
  Amino acid analysis: Asp 4.96 (5), Thr 3.77 (4), Ser 2.83 (3), Pro 1.12 (1), Gly 4.15 (4), Ala 3.00 (3), Val 3.89 (4), Leu 2.00 (2), Phe 3.10 (3), Lys 2.11 (2), His 0.98 (1), Arg 2.10 (2), Asu 1.12 (1).

Desalanyl-[Asu$^{2,7}$]-protected-c-CGRP-MBHA-resin was obtained by the following procedure:

Solid phase peptide synthesizer: 430-A peptide synthesizer Applied Biosystems Corp.

(1) Production of PF(9-37)-MBHA-resin, i.e.

MBHA-resin (Applied Biosystems Corp., amino group: 0.61 mM/g) (0.8 g) in a reaction vessel for solid phase peptide synthesis was treated with DCM (8 ml) (4 times, each 1 min.), DCM solution (8 ml) containing 60% TFA (20 min.), DCM (4 ml) times, each 15 sec.), DMF solution (3 ml) containing DIEA (1 ml) (2 times, each 1 min.) and DMF (8 ml) (6 times, each 40 sec.), in this order, under a nitrogen gas atmosphere with stirring. The material was filtered after each treatment.

DCC (0.5 M-DCM solution) (2 ml) was added to Boc-Phe (2 mM, amino acid sequence No. 37) dissolved in DCM (5 ml) in a vessel for amino acid activation and reacted for 5 mins. The filtered reaction mixture was transferred to a vessel for concentration, and DMF (3 ml) was added therein, then DCM was distilled off under a nitrogen gas atmosphere. Further DMF (3 ml) was added, and the mixture was transferred to the above reaction vessel, then reacted for 25 mins. The reaction mixture was washed 6 times with DCM (8 ml), 20 sec. each time, and the mixture was filtered to obtain Boc-Phe-MBHA-resin.

Boc-Phe-MBHA-resin hereinabove was washed 4 times with DCM (8 ml, each 1 min.) in the reaction vessel and filtered. 40% DCM solution (8 ml) containing 60% TFA was added thereto and stirred for 20 mins. to remove Boc. The thus-obtained resin was washed 3 times with DCM (4 ml, each 15 sec.), 2 times with DMF solution (3 ml) containing DIEA (1 ml) (each 1 min.) and 6 times with DMF (8 ml, each 40 sec.), in this order, and filtered.

DCC (0.5 M-DCM solution) (2 ml) was added to Boc-Ala (2 mM, amino acid sequence No. 36) dissolved in DCM (5 ml) in a vessel for amino acid activation and reacted for 5 mins., then treated the same as Boc-Phe hereinabove. The reaction mixture was concentrated after adding DMF under a nitrogen gas atmosphere, transferred into a reaction vessel and reacted for 20 mins. washed 6 times with DCM (8 ml, each 20 sec.) and filtered to obtain Boc-Ala-Phe-MBHA-resin.

Subsequently, amino acids (sequence from Nos. 9 to 35) were subjected to a coupling reaction to obtain PF(9-37)-MBHA-resin.

The protected amino acids used in the process are as follows:

| Amino Acid No. | Protected Amino Acid | Amount Used (mM) |
|---|---|---|
| 35 | Boc-Lys (Cl-Z) | 2 |
| 34 | Boc-Ser (Bzl) | 2 |
| 33 | Boc-Gly | 2 |
| 32 | Boc-Val | 2 |
| 31 | Boc-Asn | 2 × 2 |
| 30 | Boc-Thr (Bzl) | 2 |
| 29 | Boc-Pro | 2 |
| 28 | Boc-Val | 2 |
| 27 | Boc-Phe | 2 |
| 26 | Boc-Asn | 2 × 2 |
| 25 | Boc-Asn | 2 × 2 |
| 24 | Boc-Lys (Cl-Z) | 2 |
| 23 | Boc-Gly | 2 |
| 22 | Boc-Val | 2 |
| 21 | Boc-Gly | 2 |
| 20 | Boc-Gly | 2 |
| 19 | Boc-Ser (Bzl) | 2 |
| 18 | Boc-Arg (Tos) | 2 × 2 |
| 17 | Boc-Ser (Bzl) | 2 |
| 16 | Boc-Leu | 2 |
| 15 | Boc-Phe | 2 |
| 14 | Boc-Asp (OBzl) | 2 |
| 13 | Boc-Ala | 2 |
| 12 | Boc-Leu | 2 |
| 11 | Boc-Arg (Tos) | 2 × 2 |
| 10 | Boc-His (Tos) | 2 |
| 9 | Boc-Thr (Bzl) | 2 |

In the above solid phase synthesis, when Asn and Arg were used, DCC solution (2 ml) and HOBt solution (0.5 M-DMF solution) (2 ml) were added t the amino acids (2 mM) in a mixture of DMF-DCM (3:1) (4 ml), the mixture was reacted for 1 min., then treated the same as the other amino acids. The mixture was transferred into a reaction vessel for the coupling reaction, washed with DCM and filtered. Further DCC solution (2 ml) and HOBt solution (0.5 M-DMF solution) (2 ml) were added again to the amino acids (2 mM) in a mixture of DMF-DCM (3:1) (4 ml), the mixture was reacted for 25 mins., and then the mixture was transferred into a reaction vessel for the coupling reaction according to the so-called double coupling method.

(2) Production of desalanyl-[Asu$^{2,7}$]-protected-c-CGRP (3-37)-MBHA-resin:

4 N-hydrogen chloride (0.93 ml) in dioxane was added with cooling at −40° C. to cyclic PF(3-8)[10] of the formula (220 mg) dissolved in DMF (10 ml), and isoamylnitrite (60 μl) at −30° C. was added thereto. After 30 mins., and after a negative hydrazine test, triethylamine (520 μl) was added with cooling at −70° C. to neutralize the reaction mixture. PF(9-37)-MBHA-resin (1.13 g) was added thereto, and further triethylamine (90 μl) was added. The mixture was stirred at −20° C. ~ −10° C. for 5 hours, then stirred at 4° C. overnight. The reaction mixture was filtered by suction, washed with DMF (10 ml), 0.1 M acetic acid (10 ml) and ethanol (10 ml), in that order, and dried in vacuo to obtain desalanyl-[Asu$^{2,7}$]-protected-c-CGRP (3-37)-MBHA-resin (1.09 g).

A cyclic PF(3-8) [10] hereinabove was prepared by the following method.

(3) Production of cyclic-protected PF(3-8):

p-Nitrophenyl trifluoroacetate (5.7 equivalents) was added to Boc-Asn-Thr(Bzl)-Ala-Thr(Bzl)-Asu-Val-OMe [7] (3.4 g) dissolved in pyridine (50 ml) and the mixture was stirred at 45° C. for 4 hour. After distilling off the pyridine, ether was added thereto and the precipitated material was collected. Boc was removed by adding TFA (30 ml), which was distilled off in vacuo. Ether was added thereto and the precipitate was collected. The precipitate dissolved in DMF (82 ml) was added dropwise to pyridine (2.3 lit.) at 45° C., and the mixture was stirred at 50° C. for 6 hours and at room temperature overnight. Pyridine was distilled off in vacuo. 0.5% Aqueous sodium bicarbonate (100 ml) was added to the residue, and the thus-formed precipitate was washed with water completely, then dried in desiccator to obtain cyclic protected PF(3-8) [8] (3.26 g).

(4) Cyclic PF(3-8):

Anisole (1.5 ml) was added to cyclic protected PF(3-8) [8] (1.48 g). Anhydrous hydrogen fluoride (15 ml) was added thereto and the mixture was stirred at 0° C. for 1 hour. After distilling off anhydrous hydrogen fluoride in vacuo, the residue was washed with ether to obtain a white powder (1.15 g). 0.1 M acetic acid (9 ml) was added to the powder dissolved in acetic acid (3 ml) and the material was charged on a column of CHP-20 (3.2×25 cm), packed with 0.1 M acetic acid containing 33% DMF and eluted by linear gradient elution with 33% acetic acid (700 ml)~33% acetic acid containing 70% DMF (700 ml). Fractions (each 10 ml) Nos. 32–49 were collected, and the DMF was distilled off and freeze dried to obtain as a white powder cyclic PF(3-8) [9] (600 mg).

Amino acid analysis: Asp 0.99 (1), Thr 1.95 (2), Ala 1.00 (1), Val 1.01 (I), Asu 1.07 (1).

(5) Cyclic PF(3-8) [10]

Cyclic PF(3-8) [9] (600 mg) in THF (20 ml) was dissolved with heating at .60° C. and held at 30° C. NH$_2$NH$_2$.H$_2$O (2 ml) was added thereto and the mixture was stirred at room temperature for 6 hours. THF (20 ml) and DMF (10 ml) were added thereto and the material was stirred overnight. After distilling off the solvent in vacuo, the residue was dissolved in acetic acid (5 ml), and water (15 ml) was added thereto, and the material was charged on a column of CHP-20 (2.8×16.0 cm), and eluted by linear gradient elution with 0.1 M acetic acid (300 ml)~0.1 M acetic acid containing 40% acetonitrile (300 ml). Fractions (each 9.6 ml) Nos. 46–56 were collected, and freeze dried to obtain a white powder cyclic PF(3-8) [10](224 mg).

Figure 5:
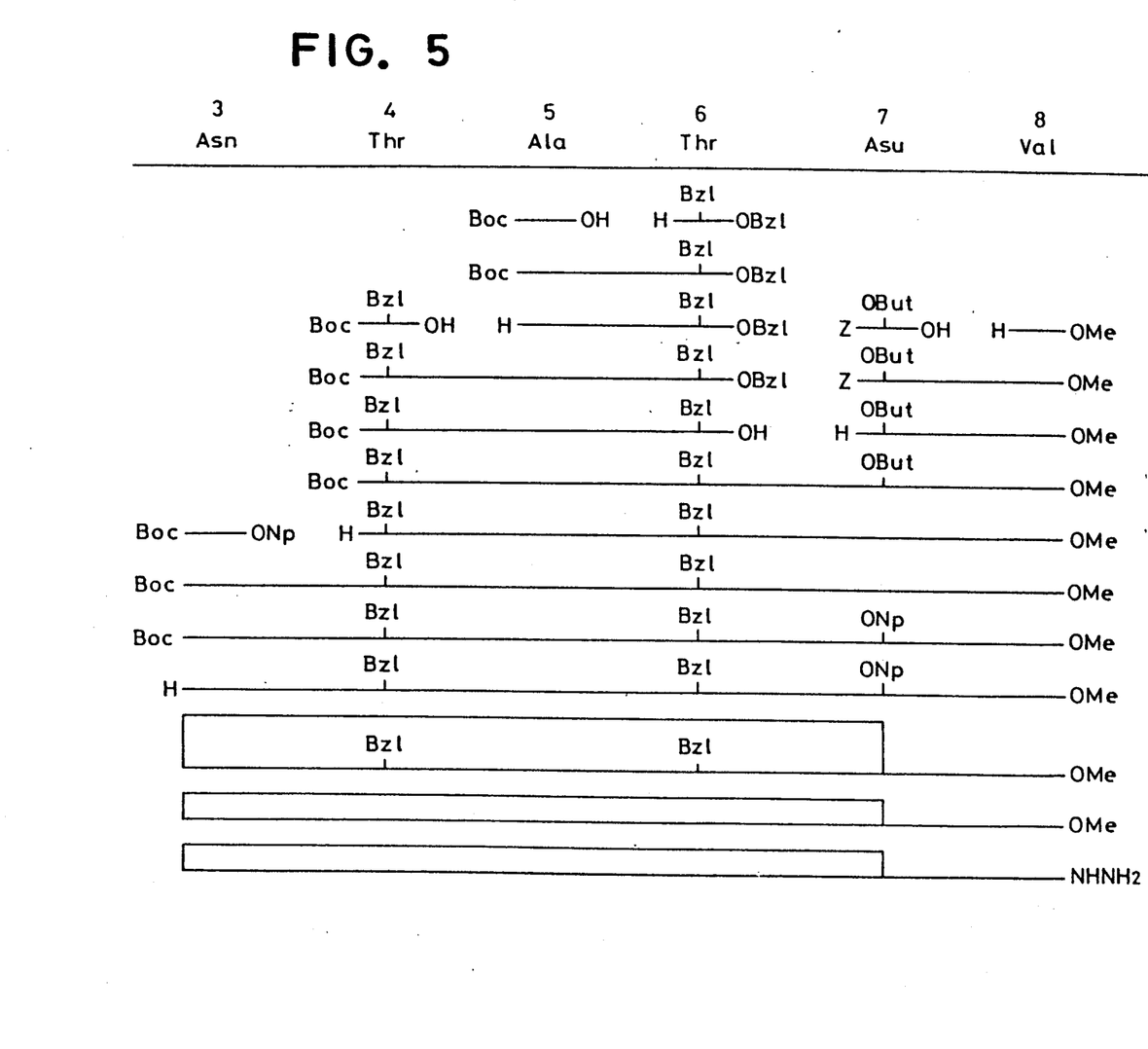
FIGS. 5 and 6 are process charts for the synthesis of intermediate peptide fragments (3-8).

The above Boc-Asn-Thr(Bzl)-Ala-Thr(Bzl)-Asu-Val-OMe [7] was produced according to the process illustrated in the production process chart for a peptide fragment (3-8) in FIG. 5.

The physico-chemical properties of the intermediate peptide fragments are as follows:

(1) PF(5-6); Boc-Ala-Thr (Bzl)-OBzl. TLC: $Rf_1$; 0.93. m.p.: 89°–95° C. Amino acid analysis: Thr 1.00 (1), Ala 1. $[\alpha]_D^{26.5}$: 10.75 (c=0.99, DMF).

(2) PF(4-6); Boc-Thr (Bzl)-Ala-Thr (Bzl)-OBzl. TLC: $Rf_1$; 0.73. m.p.: 92°–94° C. Amino acid analysis: Thr 1.97 (2), Ala 1. $[\alpha]_D^{26.5}$: 5.42 (c=1.00, DMF).

(3) PF(4-6); Boc-Thr (Bzl)-Ala-Thr (Bzl)-OH. TLC: $Rf_1$; 0.32. m.p.: 54°–58° C. Amino acid analysis: Thr 1.86 (2), Ala 1. $[\alpha]_D^{26.5}$: 24.20 (c=1.03, DMF).

(4) PF(7-8); Z-Asu (OBut)-Val-Ome. TLC: $Rf_1$; 0.90. m.p.: oily at room temperature.

(5) PF(7-8); H-Asu (OBut)Val-OMe. TLC: $Rf_1$; 0.25. m.p.: oily at room temperature.

(6) PF(4-8); Boc-Thr (Bzl)-Ala-Thr (Bzl)-Asu (OBut)-Val-OMe. TLC: $Rf_1$; 0.64. m.p.: 107°–113° C. Amino acid analysis: Thr 1.83 (2), Ala 1.00 (1), Val 1.05 (1), Asu 1.18 (1). $[\alpha]_D^{26.5}$: 5.46 (c=1.03, DMF).

(7) PF(3-8) [7]: TLC: $Rf_2$; 0.54. m.p.: 216°–218° C. Amino acid analysis: Asp 1.00 (1), Thr 1.92 (2), Ala. 1.00 (1), Val 1.00 (1), Asu 1.06 (1).

EXAMPLE 2

Production of desalanyl-[$Asp^3$,$Asu^{2,7}$]-c-CGRP: Anisole (1 ml) was added to desalanyl-[$Asp^3$,$Asu^{2,7}$]-protected-c-CGRP (3-37)-MBHA-resin of the formula His—Arg(Tos)—Leu—Ala—Asp(OBzl)—Phe—Leu—

Ser(Bzl)—Arg(Tos)—Ser(Bzl)—Gly—Gly—Val—Gly—

Lys(Cl—Z)—Asn—Asn—Phe—Val—Pro—Thr(Bzl)—Asn—

Val—Gly—Ser(Bzl)—Lys(Cl—Z)—Ala—Phe—

-MBHA-resin (1.09 g). Anhydrous hydrogen fluoride (25 ml) was added thereto and the mixture was stirred at 0° C. for 1 hour. After distilling off anhydrous hydrogen fluoride in vacuo, the residue was washed with ether and 0.1 M acetic acid (20 ml) was added thereto to extract the peptide. The extract was passed through a Dowex WGR (trademark) column (2.8×16 cm) and eluted with 0.1 M acetic acid (60 ml). The eluate was freeze dried to obtain a white powder (410 mg). The powder was charged on a column of carboxymethyl cellulose (2.8×14 cm) and was subjected to linear gradient elution with 0.01 M aqueous ammonium acetate (pH 4.5, 300 ml)~0.5 M aqueous ammonium acetate (pH 5.9, 300 ml). Samples (100 μl) from the fractions (each 10 ml) were measured colorimetrically by the Folin-Lolly method at 750 nm. Fractions Nos. 29-31 were collected and charged on a column (2.8×6.5 om) of CHP-20 resin (trademark, Mitsubishi Kasei Kogyo), and eluted by linear gradient elution with 0.1 M aqueous acetic acid containing 25% acetonitrile (150 ml)~0.1 M aqueous acetic acid containing 40% acetonitrile (150 ml). Fractions (each 6.4 ml) Nos. 10-12 were collected and freeze dried to obtain a white powder (18.2 mg). This powder was purified by reverse phase HPLC to obtain purified desalanyl-[$Asp^3$,$Asu^{2,7}$]-c-CGRP (2.8 mg).

Column: Nucleosil $5C_{18}$.

Buffer: 0.1% TFA-acetonitrile (a gradient elution with acetonitrile concentration from 28 to 38% for 25 minutes)

Flow: 2.5 ml/min.

Fraction: collected at a peak at retention time 17.7 min.

Physical properties: pI: more than 10.25. $[\alpha]_D^{26.5}$: −56.8 (c=0.091, 0.1 M acetic acid)

Amino acid analysis: Asp 4.91 (5), Thr 3.80 (4), Ser 2.80 (3), Pro 1.03 (1), Gly 4.05 (4), Ala 3.00 (3), Val 3.80 (4), Leu 1.99 (2), Phe 3.08 (3), Lys 2.08 (2), His 0.92 (1), Arg 2.03 (2), Asu 1.09 (1).

Desalanyl-[$Asp^3$,$Asu^{2,7}$]-protected-c-CGRP-MBHA-resin was obtained by the following procedure:

(1) PF(9-37)-MBHA-resin was produced by the same procedure as in Example 1.

(2) Production of desalanyl-[$Asp^3$,$Asu^{2,7}$]-protected-c-CGRP (3-37)-MBHA-resin:

4 N-hydrogen chloride (0.93 ml) in dioxane was added with cooling at −40° C. to cyclic PF(3-8) [14] of the formula (250 mg) dissolved in DMF (10 ml), and isoamylnitrite (60 μl) at −30° C. was added thereto. After 30 mins., confirming the negative hydrazine test, triethylamine (520 μl) was added with cooling at −70' C. to neutralize the reaction mixture. PF(9-37)-MBHA-resin (1.13 g) was added thereto, further triethylamine (90 μl) was added, and the mixture was stirred at −20° C.~−10° C. for 5 hours, then stirred at 4° C. overnight. The reaction mixture was filtered by suction, washed with DMF (10 ml), 0.1 M acetic acid (10 ml) and ethanol (10 ml), in this order, and dried in vacuo to obtain desalanyl-[$Asp^3$,$Asu^{2,7}$]-protected-c-CGRP (3-37)-MBHA-resin (1.09 g).

A cyclic PF(3-8) [14] hereinabove was prepared by the following method:

(3) Production of cyclic protected PF(3-8):

p-Nitrophenyl trifluoroacetate (7 equivalents) was added to Boc-Asp(OBzl)-Thr(Bzl)-Ala-Thr(Bzl)-Asu-Val-OMe [11] (3.2 g) dissolved in pyridine (40 ml) and the mixture was stirred at 45° C. for 3 hours. After distilling off the pyridine, ether was added thereto and the precipitated material was collected. The Boc was removed by adding TFA (30 ml), which was distilled off in vacuo. Ether was added thereto and the precipitate was collected. The precipitate dissolved in DMF (70 ml) was added dropwise to pyridine (2 lit.) at 45° C., and the mixture was stirred at 50° C. for 7 hours and at room temperature overnight. The pyridine was distilled off in vacuo. The residue was extracted with chloroform (400 ml) to obtain cyclic protected PF(3-8) [12] (2.62 g).

(4) Cyclic PF(3-8):

CO—Asp—Thr—Ala—Thr—NHCH—CO—Val—OMe[13]

Anisole (1 ml) was added to cyclic protected PF(3-8) [12] (2.67 g). Anhydrous hydrogen fluoride (15 ml) was added thereto with cooling at 0° C. and the mixture was stirred for 1 hour. After distilling off anhydrous hydrogen fluoride in vacuo, the residue was washed with ether to obtain a white powder (1.75 g). 0.1 M acetic acid (10 ml) was added to this powder dissolved in DMF (10 ml) and the material was charged on a column of CHP-20 (3.2×32 cm), packed with 0.1 M acetic acid containing 20% DMF and eluted by linear gradient elution with 0.1 M acetic acid (500 ml) containing 20% DMF~0.1 M acetic acid containing 66% DMF (500 ml). Fractions (each 14.8 ml) Nos. 54–63 were collected, and dried in vacuo to obtain as a white powder cyclic PF(3-8) [13] (670 mg). m.p.: 154°–160° C.

Amino acid analysis: Asp 0.98 (1), Thr 1.90 (2), Ala 1.00 (1), Val 0.96 (1), Asu 1.07 (1). Mass spectrum: 673(M+) (theoretical value 672.71).

(5) Cyclic PF(3-8) [14]

Cyclic PF(3-8) [13] (800 mg) in THF (25 ml) was dissolved with heating and cooled to 30° C. $NH_2NH_2.H_2O$ (2 ml) was added thereto and the mixture was stirred at room temperature for 6 hours. DMF (10 ml) was added thereto and the mixture was stirred overnight. After distilling off the solvent in vacuo, the residue was dissolved in 0.1 M acetic acid (15 ml), and charged on a column of CHP-20 (2.6×13.0 cm), and eluted by linear gradient elution with 0.1 M acetic acid (300 ml)~-0.1M acetic acid containing 33% acetonitrile (300 ml). Fractions (each 7.9 ml) Nos. 26–40 were collected, and freeze dried to obtain as a white powder cyclic PF(3-8) [14] (502 mg).

Figure 6:
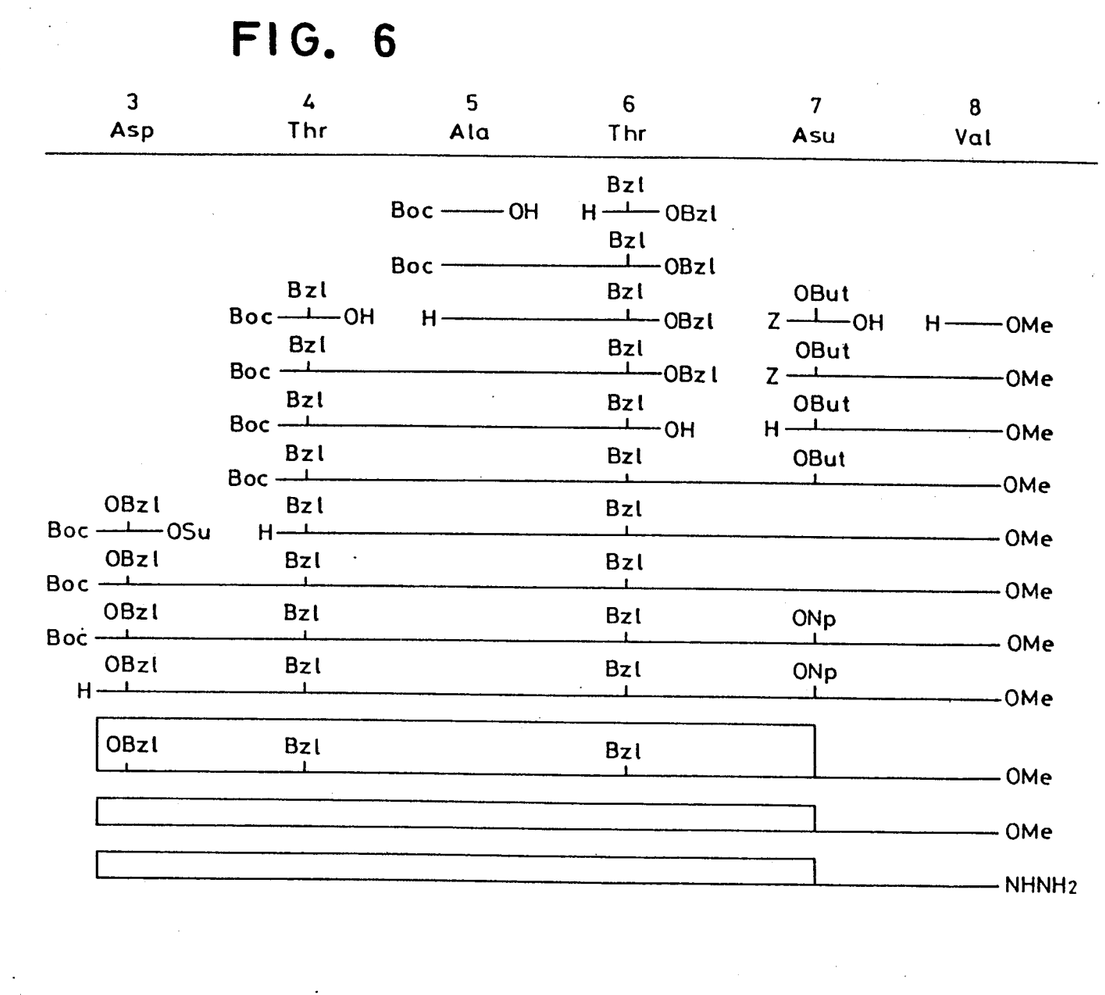

The above Boc-Asp(OBzl)-Thr(Bzl)-Ala-Thr(Bzl)-Asu-Val-OMe [11] was produced according to the process illustrated in the production process chart for a peptide fragment (3-8) in FIG. 6.

The physico-chemical properties of the above peptide fragment [11] are as follows:

TLC $Rf_2$; 0.58

Amino acid analysis: Asp 1.04(1), Thr 2.04(2), Ala 1.00(1), Val 1.06 (1), Asu 1.25 (1).

EXAMPLE 3

Production of desalanyl-deamino-c-CGRP:

Anisole (4 ml), dimethylsulfide (4 ml) and ethanedithiol (0.8 ml) were added to protected-desalanyl-deamino-c-CGRP-MBHA-resin of the formula Mbzl—S—(CH₂)₂—CO—Asn—Thr—(Bzl)—Ala—Thr(Bzl)—

Cys(MBzl)—Val—Thr(Bzl)—His—Arg(Tos)—Leu—Ala—

Asp(OBzl)—Phe—Leu—Ser(Bzl)—Arg(Tos)—Ser(Bzl)—Gly—

Gly—Val—Gly—Lys(Cl—Z)—Asn—Asn—Phe—Val—Pro—

Thr(Bzl)—Asn—Val—Gly—Ser(Bzl)—Lys(Cl—Z)—Ala—Phe—

MBHA-resin (2.65 g). Anhydrous hydrogen fluoride (40 ml) was added thereto and the mixture was stirred at 0° C. for 1 hour. After distilling off anhydrous hydrogen fluoride in vacuo, the residue was washed with ether and 20% acetic acid (50 ml) was added thereto to extract the peptide. The extract was passed through a Dowex WGR (trademark) column (2.5×15 cm) and eluted with 1 M acetic acid (160 ml). The eluate was freeze dried to obtain a white powder (780 mg). This powder (150 mg) was dissolved in 50 mM $Na_2HPO_4$ buffer (pH 7.5, 10 ml) containing 8 M urea and 5 mM dithiothreitol and the solution was stirred at room temperature for 1 hour. The reaction mixture was diluted with 50 mM $Na_2HPO_4$ buffer (pH 7.5, 1125 ml) and an aqueous solution of 20 mM $K_3Fe(CH)_6$ (8 ml) was added thereto.

The solution was charged on a column of CHP-20P resin (trademark, Mitsubishi Kasei Kogyo) (2.5×10 cm) and was subjected to linear gradient elution with 0.1 N aqueous formic acid containing 5% acetonitrile (500 ml)~0.1 N aqueous formic acid containing 45% acetonitrile (500 ml).

Samples (100 μl) from the fractions (each 10 ml) were measured colorimetrically by the Folin-Lolly method at nm. Fractions Nos. 46–53 were collected and freeze dried to obtain the white powder product (35 mg). This powder dissolved in 0.1 M acetic acid was charged on a column (1.6×45 cm) of Sephadex G-25 Fine, and eluted with 0.1 M aqueous acetic acid. Fractions (each ml) Nos. 5–15 were collected and freeze dried to obtain a white powder product (31 mg). This powder was purified by reverse phase HPLC as hereinbelow to obtain purified desalanyl-deamino-c-CGRP (10.0 mg).

Column: YMC-GEL ODS S-5 AM type (20 mmID×250 mm).

Buffer: 0.1% TFA-acetonitrile (a gradient elution with acetonitrile concentration from 27 to 40% for 30 minutes)

Flow: 7 ml/min.

Fraction: collected at a peak at retention time 17.3 min.

Physical properties: pI: more than 10.25. $[\alpha]_D^{26.5}$: −60.46 (c=0.086, 0.1 M acetic acid)

Amino acid analysis (6N-HCl hydrolysate): Asp 4.75 (5), Thr 3.62 (4), Ser 2.74 (3), Pro 1.01 (1), Gly 3.85 (4), Ala 3.00 (3), Val 3.70 (4), Leu 1.94 (2), Phe 2.83 (3), Lys 2.04 (2), His 0.95 (1), Arg 1.89 (2).

The above protected-desalanyl-deamino-c-CGRP-MBHA-resin was obtained by the following procedure:

Solid phase peptide synthesizer, 430-A peptide synthesizer, Applied Biosystems Corp. was used.

MBHA-resin (Applied Biosystems Corp., amino group: 0.48 mM/g) (1.0 g) in a reaction vessel for solid phase peptide synthesis was treated with DCM (8 ml) (4 times, each 1 min.), DCM solution (8 ml) containing 60% TFA (20 min.), DCM (4 ml) (3 times, each 15 sec.), DMF solution (3 ml) containing DIEA (1 ml) (2 times, each 1 min.) and DMF (8 ml) (6 times, each 40 sec.) in this order under a nitrogen gas atmosphere with stirring and the material was filtered after each treatment.

DCC (0.5 M-DCM solution) (2 ml) was added to BocPhe (2 mM, amino acid sequence No. 37) dissolved in DCM (5 ml) in a vessel for amino acid activation and the mixture was reacted for 5 mins. The filtered reaction mixture was transferred to a vessel for concentration, and DMF (3 ml) was added thereto, then the DCM was distilled off under a nitrogen gas atmosphere. Further DMF (3 ml) was added thereto, and the mixture was transferred to the above reaction vessel, then subjected to reaction for 25 mins. The reaction mixture was washed 6 times with DCM (8 ml) for 20 sec. each time, and filtered to obtain Boc-Phe-MBHA-resin.

Boc-Phe-MBHA-resin hereinabove was washed 4 times with DCM (8 ml, each 1 min.) in the reaction vessel and filtered. 40% DCM solution (8 ml) containing 60% TFA was added thereto and the mixture was stirred for 20 mins. to remove Boc. The thus-obtained resin was washed 3 times with DCM (4 ml, each 15 sec.), 2 times with DMF solution (3 ml) containing DIEA (1 ml) (each 1 min.) and 6 times with DMF (8 ml, each 40 sec.), in this order, and filtered.

DCC (0.5 M-DCM solution) (2 ml) was added to Boc-Ala (2 mM, amino acid sequence No. 36) dissolved in DCM (5 ml) in a vessel for amino acid activation and reacted for 5 mins., then treated the same as the Boc-Phe hereinabove. The reaction mixture was concentrated after adding DMF, under a nitrogen gas atmosphere, transferred into a reaction vessel and reacted for 20 mins., washed 6 times with DCM (8 ml, each 20 sec.) and filtered to obtain Boc-Ala-Phe-MBHA-resin.

Subsequently, amino acids (sequence from Nos. 3 to 35) were subjected to a coupling reaction and the peptide acylated with MBzl-β-mercaptopropionic acid at the final stage of reaction to obtain protected-desalanyl-deamino-c-CGRP-MBHA-resin.

The protected amino acids used in the process are as follows:

| Amino Acid No. | Protected Amino Acid | Amount Used (mM) |
| --- | --- | --- |
| 35 | Boc-Lys (Cl-Z) | 2 |
| 34 | Boc-Ser (Bzl) | 2 |
| 33 | Boc-Gly | 2 |
| 32 | Boc-Val | 2 |
| 31 | Boc-Asn | 2 × 2 |
| 30 | Boc-Thr | 2 |
| 29 | Boc-Pro | 2 |
| 28 | Boc-Val | 2 |
| 27 | Boc-Phe | 2 |
| 26 | Boc-Asn | 2 × 2 |
| 25 | Boc-Asn | 2 × 2 |
| 24 | Boc-Lys (Cl-Z) | 2 |
| 23 | Boc-Gly | 2 |
| 22 | Boc-Val | 2 |
| 21 | Boc-Gly | 2 |
| 20 | Boc-Gly | 2 |
| 19 | Boc-Ser (Bzl) | 2 |
| 18 | Boc-Arg (Tos) | 2 × 2 |
| 17 | Boc-Ser (Bzl) | 2 |
| 16 | Boc-Leu | 2 |
| 15 | Boc-Phe | 2 |
| 14 | Boc-Asp (OBzl) | 2 |
| 13 | Boc-Ala | 2 |
| 12 | Boc-Leu | 2 |
| 11 | Boc-Arg (Tos) | 2 × 2 |
| 10 | Boc-His (Tos) | 2 |
| 9 | Boc-Thr (Bzl) | 2 |
| 8 | Boc-Val | 2 |
| 7 | Boc-Cys (MBzl) | 2 |
| 6 | Boc-Thr (Bzl) | 2 |
| 5 | Boc-Ala | 2 |
| 4 | Boc-Thr (Bzl) | 2 |
| 3 | Boc-Asn | 2 × 2 |
| 2 | MBzl-S-(CH$_2$)$_2$-COOH | 2 |

In the above solid phase synthesis, when Asn and Arg were used, DCC solution (2 ml) and HOBt solution (0.5 M-DMF solution) (2 ml) were added t the amino acids (2 mM) in a mixture of DMF-DCM (3:1) (4 ml), reacted for 1 min., then treated the same as the other amino acids. The reaction mixture was transferred into a reaction vessel to perform a coupling reaction, washed with DCM and filtered. Further DCC solution (2 ml) and HOBt solution (0.5 M-DMF solution) (2 ml) were added to the amino acids (2 mM) in a mixture of DMF-DCM (3:1) (4 ml), and the mixture was reacted for 25 mins. and transferred into a reaction vessel to perform coupling according to so-called double coupling method.

What is claimed is:

1. A compound of the formula

—CO—Val—Thr—His—Arg—
Leu—Ala—Asp—Phe—Leu—
Ser—Arg—Ser—Gly—Gly—
Val—Gly—Lys—Asn—Asn—
Phe—Val—Pro—Thr—Asn—
Val—Gly—Ser—Lys—Ala—
Phe—NH$_2$ wherein Y is sulfur or methylene and A is Asn or Asp, or a pharmaceutically acceptable salt thereof.

2. A compound according to claim 1 which is peptide of the formula

Arg—Leu—Ala—Asp—Phe—Leu—Ser—Arg—Ser—Gly—
Gly—Val—Gly—Lys—Asn—Asn—Phe—Val—Pro—Thr—
Asn—Val—Gly—Ser—Lys—Ala—Phe—NH$_2$ or a pharmaceutically acceptable salt thereof.

3. A compound according to claim 1 which is a peptide of the formula

Arg—Leu—Ala—Asp—Phe—Leu—Ser—Arg—Ser—Gly—
Gly—Val—Gly—Lys—Asn—Asn—Phe—Val—Pro—Thr—
Asn—Val—Gly—Ser—Lys—Ala—Phe—NH$_2$ or a pharmaceutically acceptable salt thereof.

4. A compound of the formula

Arg—Leu—Ala—Asp—Phe—Leu—Ser—Arg—Ser—Gly—
Gly—Val—Gly—Lys—Asn—Asn—Phe—Val—Pro—Thr—
Asn—Val—Gly—Ser—Lys—Ala—Phe—NH$_2$ or a pharmaceutically acceptable salt thereof.

5. A compound of the formula

Arg—Leu—Ala—Asp—Phe—Leu—Ser—Arg—Ser—Gly—
Gly—Val—Gly—Lys—Asn—Asn—Phe—Val—Pro—Thr—
Asn—Val—Gly—Ser—Lys—Ala—Phe—NH$_2$ or a pharmaceutically acceptable salt thereof.

* * * * *